United States Patent [19]

Lindkvist

[11] Patent Number: 4,895,172

[45] Date of Patent: Jan. 23, 1990

[54] GAS COLLECTION DEVICE

[76] Inventor: Erik A. Lindkvist, Korpralsvagen 38, S-902 52 Umea, Sweden

[21] Appl. No.: 58,710

[22] Filed: Jun. 4, 1987

Related U.S. Application Data

[63] Continuation of Ser. No. 783,102, Oct. 2, 1985, abandoned.

[30] Foreign Application Priority Data

Oct. 4, 1984 [SE] Sweden .................. 84 04976-6

[51] Int. Cl.$^4$ ............................................. H11B 19/00
[52] U.S. Cl. ..................................... 128/863; 128/910
[58] Field of Search ............ 128/132 R, 139, 205.28, 128/910, 206.22, 205, 119; 2/6

[56] References Cited

U.S. PATENT DOCUMENTS

| | | | |
|---|---|---|---|
| 3,315,672 | 4/1967 | Cunningham et al. | 128/139 |
| 3,529,594 | 9/1970 | Charnley | 128/910 |
| 3,747,599 | 7/1973 | Malmin | 128/910 |
| 3,804,086 | 4/1974 | Agnew | 128/146.2 |
| 3,820,536 | 6/1974 | Anspach, Jr. et al. | 128/139 |
| 3,877,691 | 4/1975 | Fosterr | 128/910 |
| 3,955,570 | 5/1976 | Hutter, III | 128/142.7 |
| 3,990,112 | 11/1976 | Ciffolillo | 128/910 |
| 4,055,173 | 10/1977 | Knab | 128/910 |
| 4,248,218 | 2/1981 | Fischer | 128/204.18 |
| 4,265,239 | 5/1981 | Fischer, Jr. et al. | 128/205.17 |
| 4,583,246 | 4/1986 | Griswold | 128/206.22 |

FOREIGN PATENT DOCUMENTS

| | | | |
|---|---|---|---|
| 556664 | 12/1974 | Switzerland | 128/139 |
| 2005547 | 4/1979 | United Kingdom . | |

*Primary Examiner*—Max Hindenburg
*Assistant Examiner*—K. M. Reichle
*Attorney, Agent, or Firm*—Fleit, Jacobson, Cohn, Price, Holman & Stern

[57] ABSTRACT

A collection device for collecting and withdrawing anesthetic or analgesic gas exhaled by a patient. The device includes a member which is applied to the patient's chin and is provided with at least one suitably shaped opening positioned adjacent the patient's mouth, which communicates through tubing with a source of suction. The opening is positioned at the patient's chin to receive gases as they are exhaled by the patient.

11 Claims, 3 Drawing Sheets

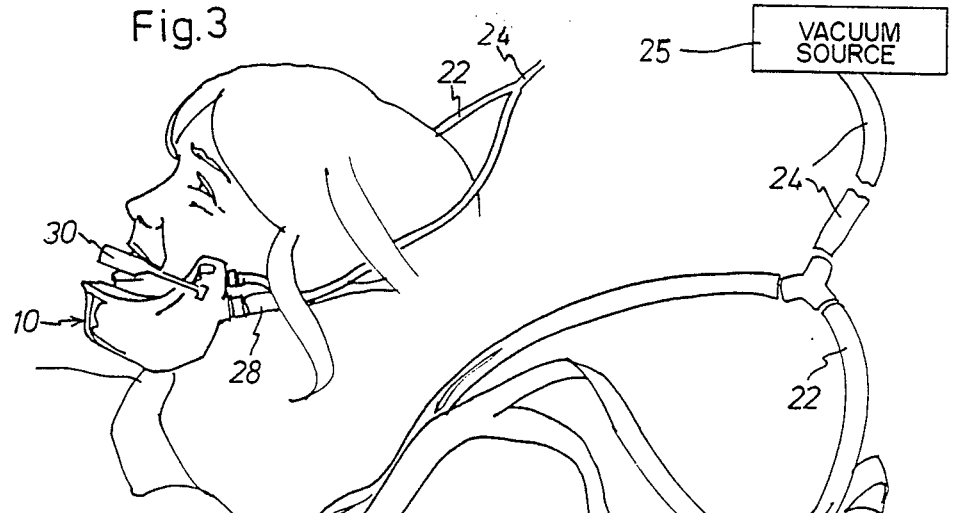
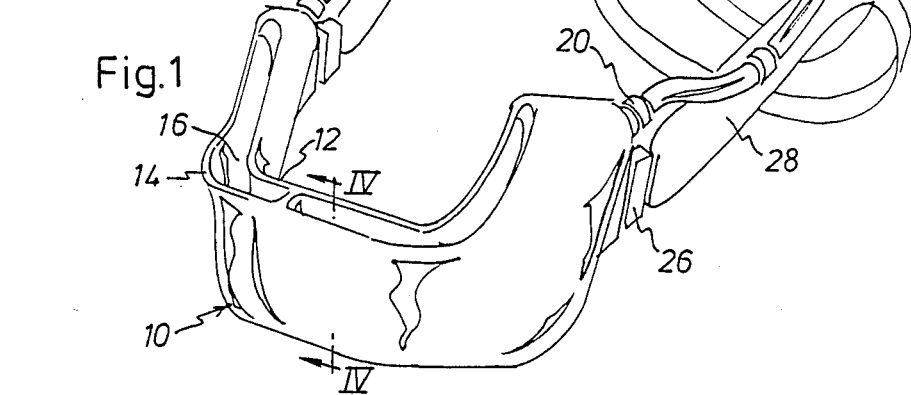

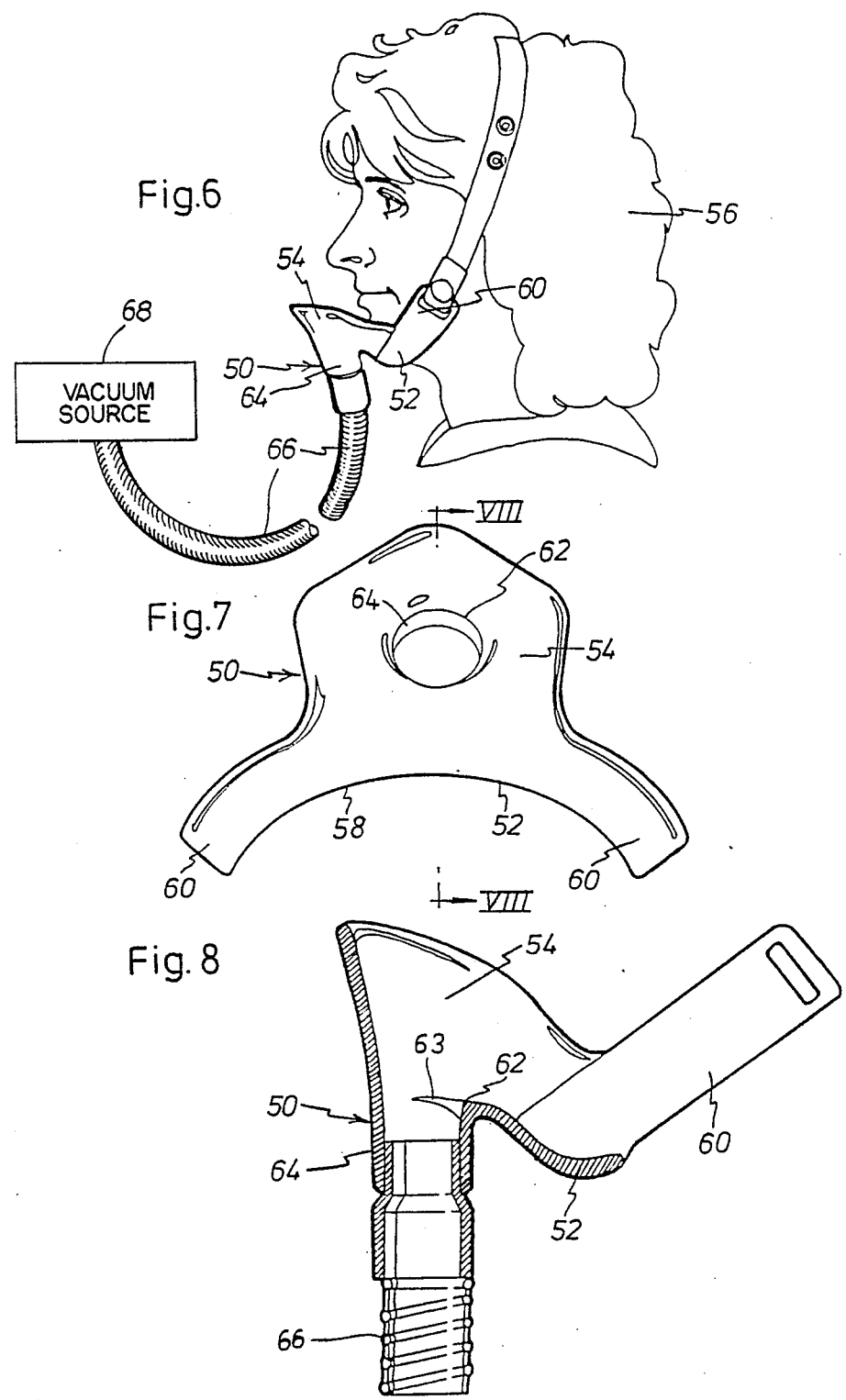

GAS COLLECTION DEVICE

This application is a continuation of application Ser. No. 783,102, filed Oct. 2, 1985 now abandoned.

BACKGROUND OF THE INVENTION

1. Field of the Invention

The present invention relates to a collecting and withdrawing device for withdrawing exhaled gases from the area around the mouth and the nose of a patient. More particularly, the invention relates to a gas collection device adapted to be carried on the chin of a patient and having an opening adjacent the patient's mouth to receive gases exhaled by the patient.

2. Description of the Prior Art

In commonly owned U.S. patent application Ser. No. 739,812, filed May 31, 1985, there is disclosed an anesthetic mask that includes a double wall to define a passageway by which anesthetic gas that leaks from around the mask can be collected to prevent it from spreading in an operating room and adversely affecting the operating room personnel. However, such an anesthetic mask that covers the mouth of the patient is not usable for the continuous administration of anesthesia in, for instance, dental surgery, or in other operations performed in the oral cavity. Furthermore, during such oral operations, the surgeon is often exposed to considerable amounts of anesthetic gas that is exhaled by the patient.

Additionally, in the administration of analgesia for the relief of pain, for instance in connection with childbirth, the above-mentioned double wall anesthetic mask has proved less useful, primarily because the device for supplying the analgesic gas, i.e., nitrous oxide or laughing-gas, is of a design different from that of masks for supplying anesthetic gas. In the supply of analgesic gas, the patient often himself adjusts the supply of the gas by holding the mask before the nose and the mouth for relatively short periods and breathing freely to inhale the gas, and then removing the mask until additional gas is needed. The air exhaled by the patient is heavily charged with the analgesic gas, and unless withdrawn its concentration in the air around the patient increases rapidly. Thus it is desirable to provide a gas collection means to prevent such contamination of the air.

Another occasion on which it is advantageous to use a gas collection means is in the post-operative recovery room of a hospital, i.e., where the patients wake up after an operation and where they remain temporarily while the effect of the anesthesia is dissipating. The air exhaled by such patients also contains substantial amounts of anesthetic gas, and such rooms can therefore have a significant concentration of such gas.

An object of this invention is to provide a gas collection device which makes it possible readily to collect and withdraw primarily anesthetic or analgesic gas borne by the exhaled breath of a patient.

BRIEF SUMMARY OF THE INVENTION

Briefly stated, in accordance with one aspect of the present invention a device is provided for collecting anesthetic or analgesic gas exhaled by a patient. The device includes collector means in the form of a concave member and includes a collection opening. The collector means is adapted to engage with and overlie a part of the chin of a patient adjacent his mouth. The opening is positioned adjacent the flow of exhaled gas that passes from the patient's mouth. Attaching means are provided to removably secure the device to the patient's chin. Conduit means extend from the collection opening to a source of reduced pressure to cause exhaled gas from the patient to be drawn into the opening and collected, to thereby reduce contamination of the air surrounding the patient by anesthetic or analgesic gases exhaled by the patient.

BRIEF DESCRIPTION OF THE DRAWINGS

One embodiment of the device according to the invention will be described in greater detail hereinbelow with reference to the accompanying drawings, in which FIG. 1 is a front perspective view of a gas collection device in accordance with the present invention;

FIG. 2 is a perspective view of a patient wearing the device;

FIG. 3 is a side view of a patient wearing the device;

FIG. 6 is a side view of another embodiment of a gas collection device in accordance with the present invention.

FIG. 7 is a top view of the embodiment of FIG. 6 as seen from the top with the device oriented as shown in FIG. 6.

FIG. 8 is a side cross-sectional view of the embodiment of FIG. 6 taken along the line 8—8 of FIG. 7.

DESCRIPTION OF THE PREFERRED EMBODIMENTS

Figure 4:
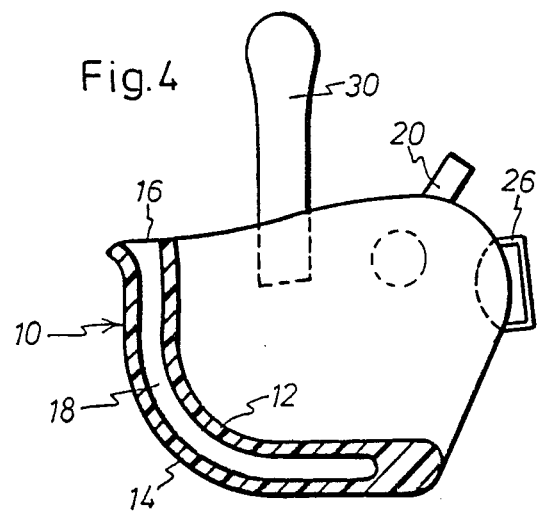
FIG. 4 is a cross-sectional view showing the construction of the device.

Referring now to the drawings, and particularly to FIG. 1, the gas collection device according to the present invention includes a substantially cup-shaped, at least partly double-walled hollow member 10 of a soft, dimensionally stable or semi-rigid, suitably transparent material. The device includes an inner wall 12 shaped to engage with and lie against the chin of a patient and an outer wall 14 spaced outwardly of the inner wall. A suction gap or slot 16 defined by outer lips of the walls 12 and 14, extends along the outer edge of the device between the chin and mouth of the user, and preferably is at least as long as the width of the mouth of a patient. Gap 16 communicates through the space between the inner and outer walls, which define an internal cavity 18 (see FIG. 4) having an open end defined by the gap or slot 16, and also having an essentially closed opposite end, with tubular connection means at the opposite end in the form of nipples 20 for connection with suction hoses 22, which merge into a common suction line 24 behind the patient's head. Suction line 24 is in communication with a vacuum pump or other source of vacuum (FIG. 1).

Hollow member 10 is also provided with attachment means 26, which can be, for example, a Velcro connection for a strap 28 intended to pass around the back of the neck of the patient to securely hold the collection device in the desired position without enclosing or obstructing the mouth and nostrils of the patient, which remain open to the surrounding atmosphere.

When the device 10 is in position against the patient's chin, as best seen in FIGS. 2 and 3, the suction gap 16 will face upwardly along the patient's face, and will be substantially aligned with the patient's nostrils, i.e., at a certain distance from and obliquely outwardly of the lower lip of the patient. Thus, by the reduced pressure produced in gap 16, air that is exhaled through the patient's nostrils and mouth can be intercepted, collected, and carried to a discharge point so that the concentration of anesthetic or analgesic gas in the air around the patient does not increase.

For a patient in a post-operative recovery room, who is often breathing quickly with his mouth open, the device 10 can also be provided with a deflecting means, such as tongue 30, of a soft, but dimensionally stable and deformable material. Tongue 30 can be bent or displaced to a desired position and can be suitably detachably secured to the device to dispose the tongue 30 substantially opposite the patient's mouth. The exhaled gas will be blocked from flowing straight out, and a turbulent movement of exhaled gas is produced instead, to reduce the outward velocity of the exhaled gas so that it can easily be drawn into the gap 16 by virtue of the reduced pressure in cavity 18.

In connection with analgesic gas administration, when the patient himself administers gas by means of a mask 32 (see FIGS. 2 and 5) that overlies his mouth and nose, the deflecting means 30 can be moved completely out of the way or detached to permit unimpeded access of the mask 32 to the patient's nose and mouth. The deflecting means 30 is principally intended for use in the application of anesthesia in conjunction with dental surgery or operations in the oral cavity.

Figure 5:
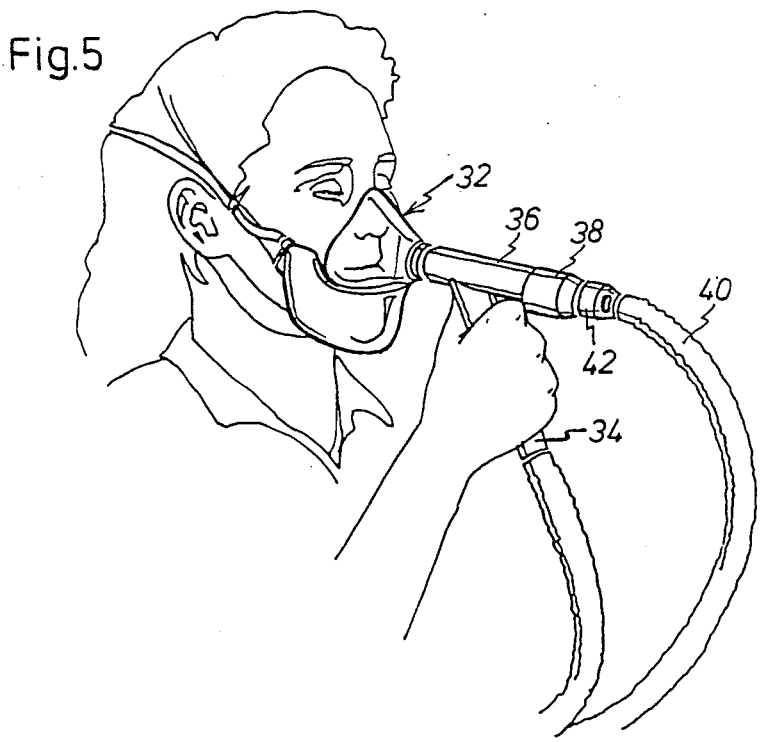
FIG. 5 is a side view of one form of mask for supplying analgesic gas and that is usable with the collection device of the present invention.

To cope with the problem of leakage of analgesic gas and with the collection of exhaled analgesic gas, i.e., laughing-gas, the mask 32 that is used can be of the design shown in FIG. 5. The mask preferably is made from a transparent material, and includes, in addition to the conventional connecting piece 34 for the laughing-gas, a further connecting piece 36, which is provided with a non-return valve 38 to which is connected a suction line 40, which is at a slightly reduced pressure. The reduced pressure is so adjusted as to compensate for flow resistance in line 40, and thus, when the patient is exhaling, he should not feel a resistance to exhalation, which would be the case if no reduced pressure existed in line 40. The non-return valve 38 is of the balanced type and is provided with an opening 42 for admitting "supplementary air." Opening 42 is disposed downstream of valve 38 as seen in the direction of suction flow. As long as the patient is inhaling laughing-gas, the non-return valve is closed, and air from the surrounding atmosphere can enter through the opening 42, such that no buildup of reduced pressure takes place in suction line 40. As soon as the patient exhales the non-return valve opens and the exhaled gas will be drawn off through suction line 40.

Another embodiment of the present invention is illustrated in FIGS. 6 through 8. In that embodiment the collection device 50 is a single wall structure that includes a chin engaging portion 52 from which a collection bowl portion 54 extends outwardly. As illustrated in FIG. 6, the chin engaging portion is positioned against the chin of the patient 56, and includes a curved central portion 58 (See FIG. 7) and two chin side pieces 60 to extend partially around the chin of the patient in an essentially U-shaped configuration, to engage the sides of the lower jaw of the patient to thereby hold the device in position. Although not shown in the drawings, a strap similar to that illustrated in FIGS. 1 through 3 can be provided to hold the collection device 50 in position.

As best seen in FIG. 8, the collection bowl portion 54 presents a hollowed-out structure of generally concave configuration that is positioned outwardly of the patient's mouth with the concave portion facing the patient, and it includes a suction opening 62, that terminates in a hose connection 64, to which a suitable suction hose 66 can be attached, in a manner similar to that of the earlier-described embodiment. Suction hose 66 is adapted to be brought into communication with a suitable source of vacuum 68 (FIG. 6).

The collection device embodiment of FIGS. 6 through 8 can also preferably be made of a soft, resilient material, such as a flexible plastic, to adapt to the shape of the chin of the patient. Additionally, the device can be opaque, or translucent, as desired.

Referring once again to FIG. 6, the position of the collection bowl 54 and the suction opening 62 relative to the mouth of the patient can be adjusted by moving the chin engaging portion either upwardly toward the patient's mouth or downwardly away from the patient's mouth, as required. In that connection, if the device is used during operations on the oral cavity, the chin engaging portion would preferably be moved downwardly to expose the mouth for improved access during the operating procedure. After the operation, and for other uses where direct oral access is not required, the chin engaging portion can be moved upwardly around the front of the chin, to cause collection bowl 54 to extend in such a manner relative to the patient's mouth that the suction opening is so positioned that the reduced pressure is sufficient to capture the exhaled breath, and thereby prevent excessive escape of anesthesia gas to the surrounding atmosphere.

Referring once again to FIG. 8, suction opening 62 formed in the collection bowl has, but for a projecting step shaped portion 63 opposite the bowl, preferably a smooth shape to provide a smooth transition from bowl portion 54 to hose connection 64, and to thereby minimize noise that might otherwise occur as a result of the flow of gases into the hose connection from the collection bowl. The step shaped portion 63 is intended to reduce radial flow of exhaled air as such radial inflow would pass directly over the lower lip of the patient and might give some discomfort. In that connection, it has been found that the embodiment illustrated in FIGS. 6 through 8, wherein, as is clearly shown in FIG. 6, the collection bowl 54 has a gas collection opening defined in part by an outer wall with an upper edge located at a level essentially corresponding to that of the mouth of the patient and spaced outward from the mouth of the patient a distance beyond the patient's nose, provides an efficient collection device that provides a zone of reduced pressure in the bowl 54 and adjacent the patient's mouth to draw in the exhaled gas, and it functions without excessive noise, and therefore permits a lower suction pressure to be applied at the suction opening. In the embodiment illustrated in FIGS. 1 through 5, on the other hand, the much larger area associated with the suction gap 16 requires a larger suction pressure to be applied to effectively collect the exhaled gas, which can increase the noise level adjacent the device. However, when the suction opening, and thereby the collection point, is positioned either at or immediately below the flow direction of gas being exhaled by the patient, a wide suction gap is not necessary, and the collection can be effected at a lower suction pressure level. Further, as will be apparent by reference to FIG. 6, the orientation of the bowl portion 54 is such as to directly capture gas exhaled through the nasal passages, and indirectly to capture gas exhaled through the mouth of the patient.

Although particular embodiments of the present invention have been illustrated and described, it will be apparent to those skilled in the art that various changes and modifications can be made without departing from the spirit of the present invention, and it is intended to cover in the appended claims all such changes and modifications that fall within the scope of the present invention.

What is claimed is:

1. A gas collection device to be worn by a patient for collecting and removing gas exhaled by the patient, from an area around the mouth and nose of the patient, comprising:

first portion means for engaging with the chin of the patient;

second concave gas collector portion means projecting from the chin engaging portion means, said gas collector portion means for positioning below the nose and adjacent the mouth of the patient and in the flow path of the gas being exhaled from the mouth and nose of the patient, enabling collection of the exhaled gas, while allowing open communication between the surrounding atmosphere and the mouth and nose of the patient, and free and ready access to the mouth and nose of the patient;

attaching means connected to the chin engaging portion means for removably securing the chin engaging portion means to the patient's chin; and gas removal conduit means connected in fluid communication with the concave gas collector portion means for removing collected gas from the concave gas collector portion means.

2. A gas collection device according to claim 1 wherein said chin engaging portion means and said concave gas collector portion means are made from a soft, dimensionally stable transparent material.

3. A gas collection device according to claim 1 wherein said attaching means includes a strap for passing around the back of the neck of the patient, and means for connecting the strap to the chin engaging portion means.

4. A gas collection device according to claim 1 wherein said gas removal conduit means includes suction hose means extending from the concave gas collector portion means for removing collected gas from the concave gas collector portion means.

5. A gas collection device according to claim 1 including gas deflecting means for extending from said concave gas collector portion means into the flow path of the gas exhaled from the mouth of the patient but still spaced from the patient's mouth, to block outward flowing exhaled gas from the mouth of the patient and to cause turbulent movement thereof, thereby facilitating collection of the exhaled gas by said gas collection portion means.

6. A gas collection device according to claim 5 wherein said deflecting means is formed from a deformable material that can be bent to orient said deflecting means in a desired position relative to the patient's mouth.

7. A gas collection device according to claim 1, further comprising side piece means extending from said chin engaging portion means for engaging respective opposite sides of the lower jaw of the patient.

8. A gas collection device according to claim 1 wherein said concave gas collector portion means comprises a gas collection bowl including a first wall portion connected to the chin engaging portion means and adapted to be positioned below the mouth of the patient, and also including a second opposite wall portion spaced from said first wall portion to define a gas collection opening therebetween and adapted to be positioned below the nose and spaced from the mouth of the patient.

9. A gas collection device according to claim 13 wherein the gas collection bowl has a portion means projecting at least partially across the gas collection opening for minimizing noise from the flow of collected gases and reducing radial flow of exhaled air over the lower lip of the patient.

10. A gas collection device to be worn by a patient for collecting and removing gas exhaled by the patient, from an area around the mouth and nose of the patient, comprising:

a housing having a first wall shaped and contoured to extend about the chin of the patient, and a second wall parallel to the first wall and connected along edges thereof to respective edges of the first wall, with the second wall spaced from the first wall so as to define an internal gas collection cavity therewith;

attaching means connected to the housing for removably securing the first wall of the housing against the patient's chin below the mouth with the second wall spaced therefrom;

the first and second walls also having edges adapted to be positioned below and extending adjacent the patient's mouth and being spaced apart to define a slot which is adapted for positioning in the flow path of the gas being exhaled from the mouth and nose of the patient, enabling collection of the exhaled gas, while allowing open communication between the surrounding atmosphere and the mouth and nose of the patient, and free and ready access to the mouth and nose of the patient; and gas removal conduit means connected to the housing in fluid communication with the cavity for removing collected gas from the cavity.

11. A gas collection device according to claim 10 including gas deflecting means for extending from said housing into the flow path of gas exhaled from the mouth of the patient but still spaced from the patient's mouth, to block outward flowing exhaled gas from the mouth of the patient and to cause turbulent movement thereof, thereby facilitating collection of the exhaled gas by said slot and said internal gas collection cavity.

* * * * *